United States Patent [19]
Kishimoto et al.

[11] Patent Number: 5,465,721
[45] Date of Patent: Nov. 14, 1995

[54] ULTRASONIC DIAGNOSTIC APPARATUS AND ULTRASONIC DIAGNOSIS METHOD

[75] Inventors: Shinji Kishimoto, Ibaraki; Masa Harashima, Kashiwa; Hiroshi Kanda, Tokorozawa; Akira Sasaki, Ichikawa; Kozi Tanabe, Kashiwa; Kenji Nosaka, Kodaira; Satoru Hanasaka, Kashiwa; Ken Ishihara, Takarazuka, all of Japan

[73] Assignee: Hitachi Medical Corporation, Tokyo, Japan

[21] Appl. No.: 400,845

[22] Filed: Mar. 8, 1995

[30] Foreign Application Priority Data

Apr. 22, 1994 [JP] Japan .................................. 6-084289
Apr. 22, 1994 [JP] Japan .................................. 6-084290
Jun. 24, 1994 [JP] Japan .................................. 6-142967
Aug. 3, 1994 [JP] Japan .................................. 6-182079

[51] Int. Cl.$^6$ ........................................... A61B 8/00
[52] U.S. Cl. .................. 128/660.07; 128/916; 128/661.1
[58] Field of Search ........................ 128/660.04, 660.05, 128/660.07, 660.02, 661.08, 661.09, 661.10, 916

[56] References Cited

U.S. PATENT DOCUMENTS 5,195,521 3/1993 Melton ............................... 128/660.02
5,322,067 6/1994 Prater et al. ........................ 128/660.07
5,409,010 4/1995 Beach et al. ........................ 128/661.09

*Primary Examiner*—George Manuel
*Attorney, Agent, or Firm*—Antonelli, Terry, Stout & Kraus

[57] ABSTRACT

A two-dimensional echogram or a tomogram (B-mode image) and a volume of an organ are displayed in real time while radiating an ultrasonic wave to the organ. The volume of the organ is obtained by first designating a plurality of line segments traversing the image of the organ on the two-dimensional echogram, by obtaining a pair of intersections between each line segment and the wall of the organ by using a signal intensity profile (A-mode image) of each line segment, by obtaining a length between the pair of intersections, and by calculating the volume by the Simpson method by using the obtained length. In order to improve the precision of volume calculation, the signal intensity profile is smoothed and the intensity is normalized. The intersections are displayed superposed upon the two-dimensional echogram to allow an operator to visually check easily whether the intersections are correctly aligned with the wall of the organ. If the B-mode image of a heart is displayed in slow motion, the signal intensity is also normalized to display the image brightly during a systole period which image otherwise is likely to become dark during the systole period.

17 Claims, 16 Drawing Sheets

$$V=(A_1+A_2+A_3)h+\frac{A_4 h}{2}+\frac{\pi}{6}h^3$$

5,465,721

ULTRASONIC DIAGNOSTIC APPARATUS AND ULTRASONIC DIAGNOSIS METHOD

BACKGROUND OF THE INVENTION

1. Field of the Invention

The present invention relates to an ultrasonic diagnostic apparatus and an ultrasonic diagnosis method, and more particularly to an improved ultrasonic diagnostic apparatus provided with a function of measuring the volume or the like of an organ.

2. Description of the Related Art

An ultrasonic diagnostic apparatus is a diagnostic apparatus by which an ultrasonic wave is radiated into a subject body and a two-dimensional echogram or the like of the body is reconstructed from reflected ultrasonic waves.

Also know nowadays is an apparatus which displays a two-dimensional echogram or a tomogram such as an image including a heart on a cathode ray tube (CRT) and can calculate the volume or the like of the heart based upon the displayed heart image.

Specifically, the volume of a heart can be displayed by designating several line segments traversing a displayed image of the heart, by a mouse or the like. In this case, the apparatus operates to read data of line segment lengths within the heart, and in accordance with the read data the heart volume is calculated by using a predetermined calculation equation.

However, with a conventional ultrasonic diagnostic apparatus constructed as above, in designating several line segments traversing the heart by using a mouse or the like, the displayed moving image is made still (freeze image).

Therefore, the calculated volume or the like is a value at some moment during the systole and diastole periods. The change in the volume during the continuous motion of the heart has been unable to be obtained in real time.

SUMMARY OF THE INVENTION

The object of the invention is to solve the above problems.

According to one embodiment, in order to calculate and display the volume of an organ in real time, two frame memories are prepared for sequentially storing data used for the reconstruction of a B-mode two-dimensional echogram or a tomogram. While data is written in one frame memory, data in the other frame memory is read and processed to calculate and display the volume.

The volume of an organ is calculated in the following manner. A line segment traversing an organ is designated on a two-dimensional echogram or a tomogram, and a pair of intersections between the line segment and the wall of the organ is obtained from the signal intensity profile (A-mode data) of the image data along the line segment. The volume is calculated, for example, by a Simpson method by using the length between the intersection pair. According to the invention, the signal intensity profile is smoothed in order to improve the precision of volume calculation. As a smoothing method, in the embodiment, an envelope line of the signal intensity profile is used or the moving average of the signal intensity profile is used. In order for an operator to check whether the obtained pair of intersections correctly correspond to the wall of an organ, the intersections are displayed substantially in real time, superposing upon a B-mode two-dimensional echogram.

In order to improve the precision of volume calculation, the signal intensity profile is normalized. The intensity of a peak of the profile is made coincident with a predetermined signal intensity reference. It is preferable to subject a profile having a small signal intensity to the normalizing process. An image of a heart picked up by ultrasonic waves has a small signal during a systole period. The image data during the systole period is therefore amplified while identifying the motion of a heart, for example, by identifying it from an electrocardiogram.

Similarly, the signal intensity of B-mode data can also be normalized. For example, since the two-dimensional echogram of a heart becomes dark during the systole period, the signal intensity is normalized so as to make the image easy to be observed.

Also in the case where B-mode display is performed in slow motion, the volume of an organ is obtained in the manner similar to the above and displayed synchronously with the motion of the organ which moves in slow motion.

The volume of an organ is displayed in the form of numerical value or graph. In the case of the graph, it is preferable to display it synchronously with the motion of the organ. To this end, the apparatus of the embodiment is provided with a monitor for monitoring the operation of an organ. For the observation of a heart, an electrocardiogram is monitored.

The invention also discloses a method of non-invasively measuring the inner pressure of a heart.

BRIEF DESCRIPTION OF THE DRAWINGS

These and other objects and technical advantages of the present invention will be readily apparent from the following description of the preferred exemplary embodiments of the invention when read in conjunction with the accompanying drawings, in which.

DETAILED DESCRIPTION OF THE PREFERRED EMBODIMENTS

1st Embodiment

Figure 1:
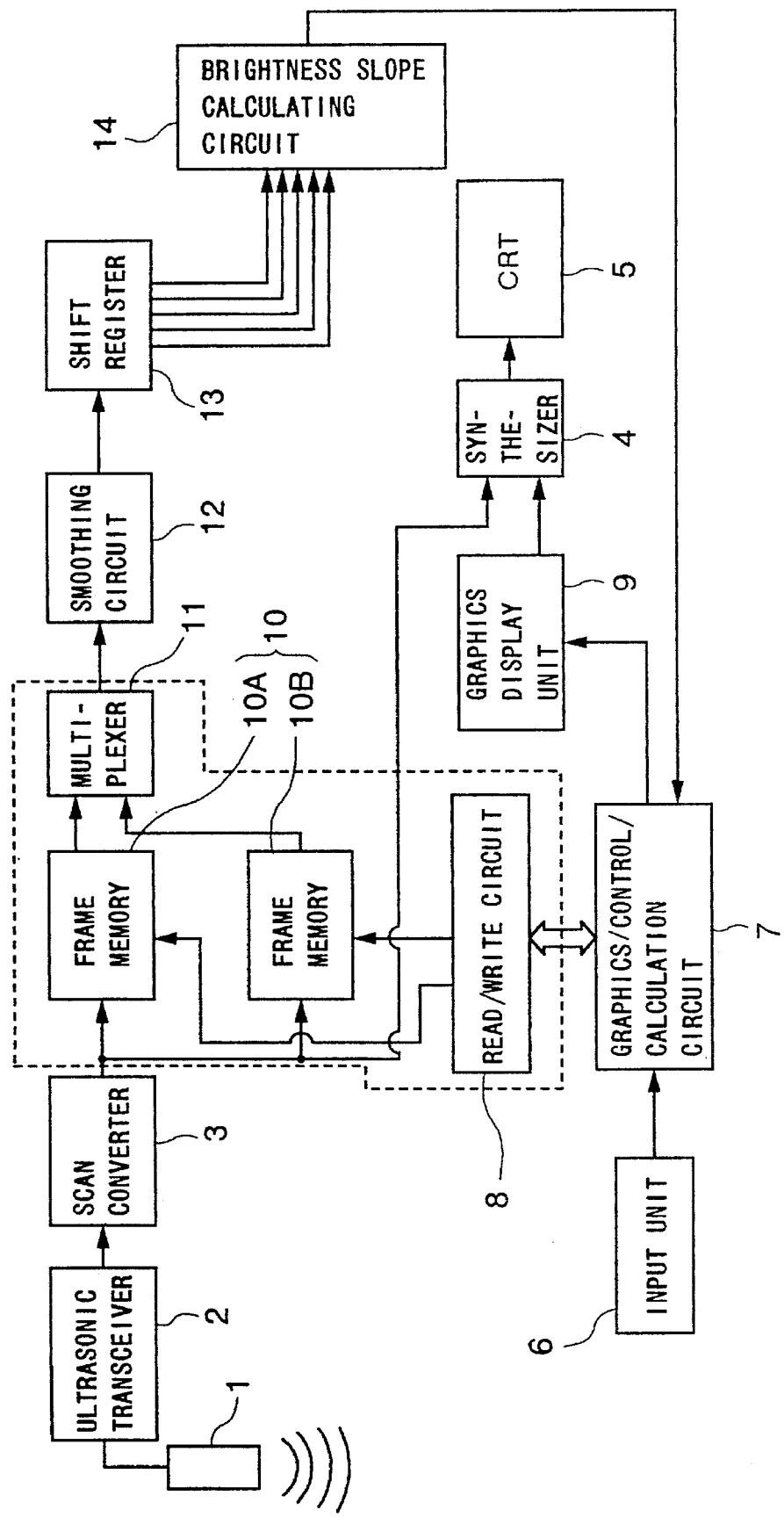
FIG. 1 is a block diagram showing the structure of an ultrasonic diagnostic apparatus according to an embodiment of the invention.

FIG. 1 is a block diagram showing the structure of an ultrasonic diagnostic apparatus according to the first embodiment of the invention.

In FIG. 1, an ultrasonic probe 1 is used by holding it against a subject body, and is a so-called sector scan type probe from which ultrasonic waves are transmitted in radial directions.

In this embodiment, a two-dimensional echogram or a tomogram including a heart image is reconstructed. Therefore, the ultrasonic probe 1 is held against the chest wall near the heart.

The ultrasonic probe 1 is driven by an ultrasonic transceiver 2 and radiates ultrasonic waves into the subject body. Ultrasonic information of reflected waves (echoes) is received by the ultrasonic transceiver 2.

The analog ultrasonic data received by the ultrasonic transceiver 2 is converted by its built-in A/D converter into digital ultrasonic data which is then supplied to a digital scan converter 3.

The digital scan converter 3 writes the digital ultrasonic data into its built-in line memory each time one or a plurality of ultrasonic beams are scanned, to thereby store image data of a tomogram or a two-dimensional echogram (B-mode).

The digital scan converter 3 supplies the image data via a synthesizer 4 to a display device 5 such as a CRT to display a two-dimensional echogram including a heart image on the screen of the display device 5.

Figure 2:
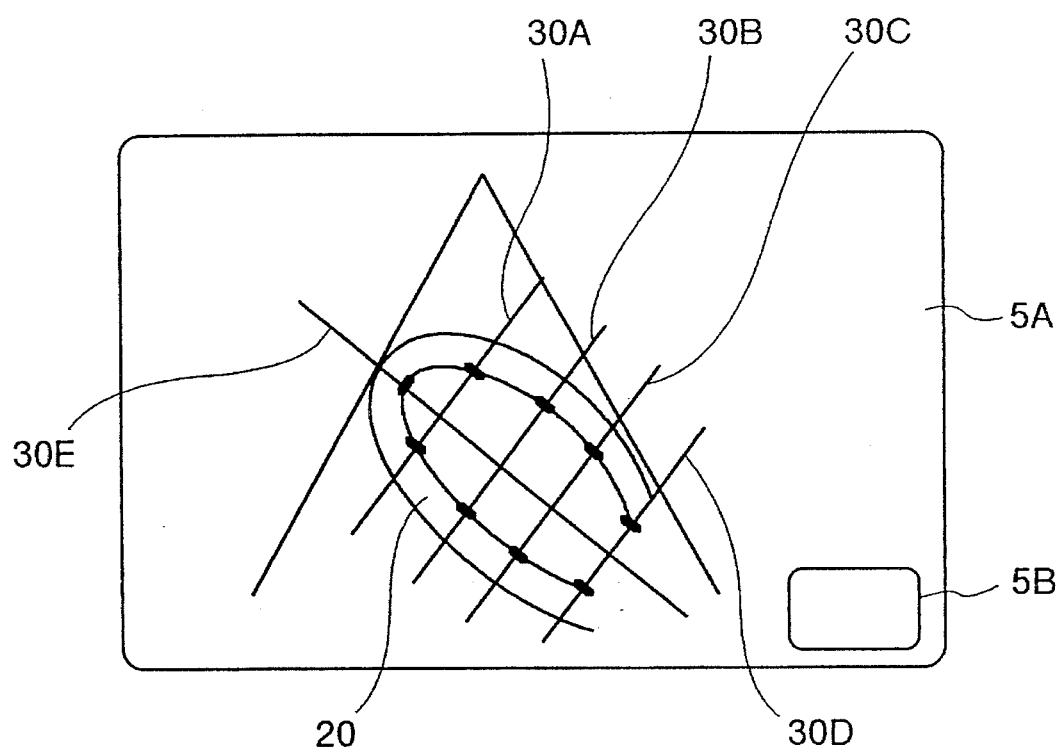
FIG. 2 is a diagram showing an example of a display on the display device of the ultrasonic diagnostic apparatus of the embodiment.

As shown in FIG. 2, a two-dimensional echogram including a heart image 20 is displayed on the screen 5A of the display device 5. Line segments 30A to 30E are adapted to be designated and displayed on the screen 5A.

Designating the line segments is performed by an input device 6 such as a mouse. Line segment information entered by the input device 6 is supplied via a graphics/control/calculation circuit 7 to a read/write circuit 8 to be described later in detail. In this embodiment, when the line segment 30E is manually set, the other line segments 30A to 30D orthogonal to the line segment 30E are automatically set at an equal interval. The number of line segments to be automatically set is preset. The narrower the interval between line segments, the more precisely the volume or capacity can be calculated. Instead of presetting the number of line segments to be automatically set, the interval between line segments may be preset.

The resultant data upon designation of the line segment from the input unit 6 is supplied via a graphics display unit 9 and the synthesizer 4 to the display device 5 to display the line segments superposed upon the two-dimensional echogram.

The line segments 30A to 30E are displayed on the display screen at fixed positions, whereas the heart images 20 of two-dimensional echogram are displayed in real time during the systole and diastole periods.

The image data is inputted from the scan converter 3 to the frame memory 10 which stores one frame of image data.

The frame memory 10 has two frame memories 10A and 10B. One frame of image data is stored in the frame memory 10A, the next frame of image data is stored in the frame memory 10B, the second next frame of image data is stored in the frame memory 10A, and so on. In this manner, the image data is stored alternately in the two frame memories. While the image data of the next frame is written on one frame memory 10A (or 10B), the image data of one frame already stored in the other frame memory 10B (or 10A) is processed in the manner to be described later and the volume or capacity value of the heart is displayed on CRT 5. In this manner, the volume or capacity of the heart is displayed substantially in real time. The data write to the frame memories 10A and 10B is performed by the read/write circuit 8.

The read/write circuit 8 reads the image data from each of the frame memories 10A, 10B. In this case, in accordance with the information of the line segments 30A to 30E entered from the input unit 6 via the graphics/control/calculation circuit 7, the read/write circuit reads the image data along each line segment 30A to 30E. That is to say, in accordance with the addresses for determining the line segments 30A to 30E, the image data is read from each of the frame memories 10A and 10B.

The image data read in the above manner from each of the frame memories 10A and 10B is supplied to a multiplexer 11 which in turn sequentially outputs the image data of each frame along each line segment 30A to 30E.

Figure 3:
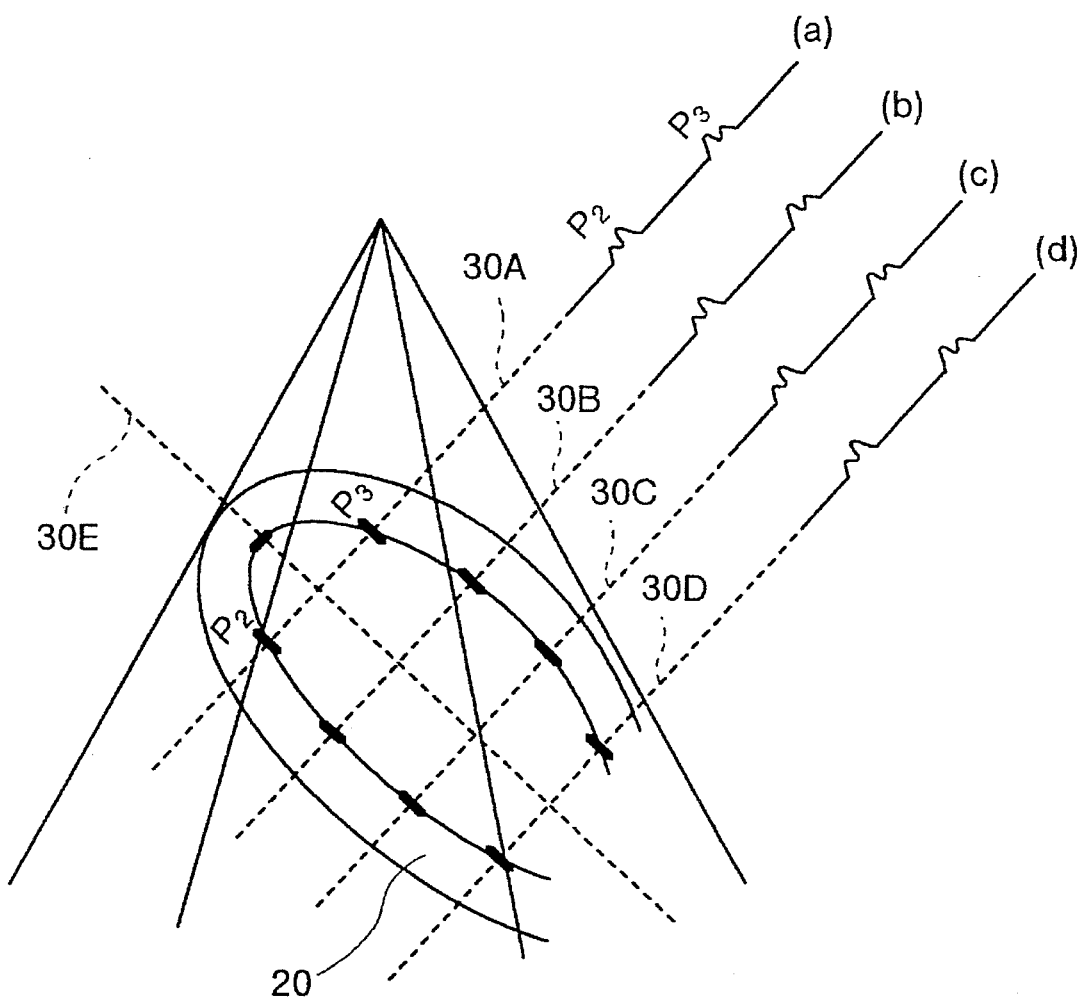
FIG. 3 is a diagram showing signal intensity profiles of pixel data on line segments designated on the display.

FIG. 3 shows the image data (A mode) of each frame along each line segment 30A to 30D. A signal intensity profile indicated at (a) in FIG. 3 is obtained for the image data along the line segment 30A, a signal intensity profile indicated at (b) in FIG. 3 is obtained for the image data along the line segment 30B, a signal intensity profile indicated at (c) in FIG. 3 is obtained for the image data along the line segment 30C, and a signal intensity profile indicated at (d) in FIG. 3 is obtained for the image data along the line segment 30D.

The signal intensity profiles of the image data along the segment lines 30A to 30E are sequentially inputted to and smoothed by a smoothing circuit 12.

Figure 4:
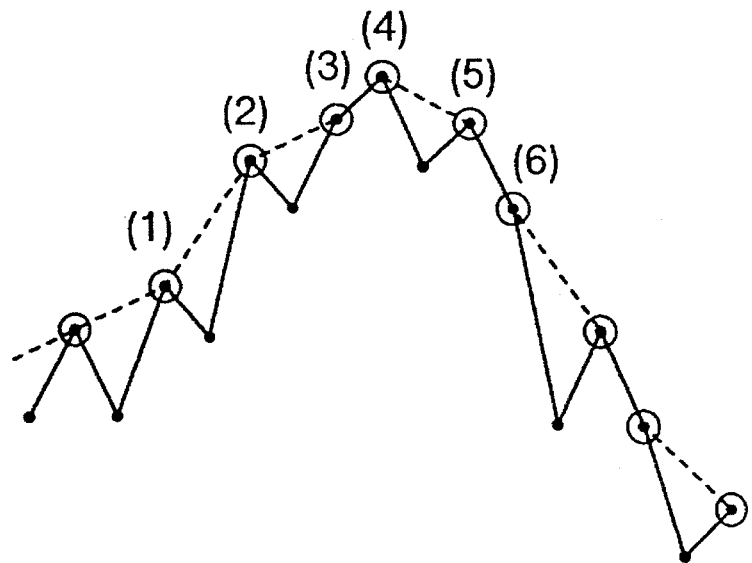
FIG. 4 is a diagram explaining an embodiment of a pixel data smoothing method.
Figure 5:
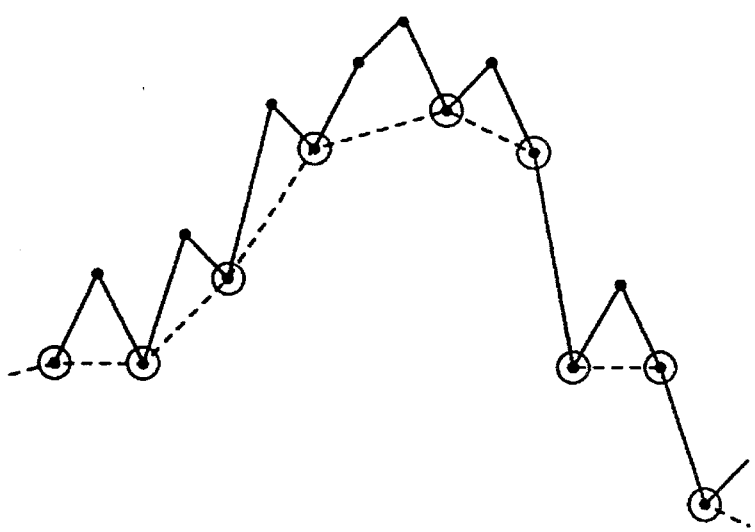
FIG. 5 is a diagram explaining another embodiment of a pixel data smoothing method.
Figure 6:
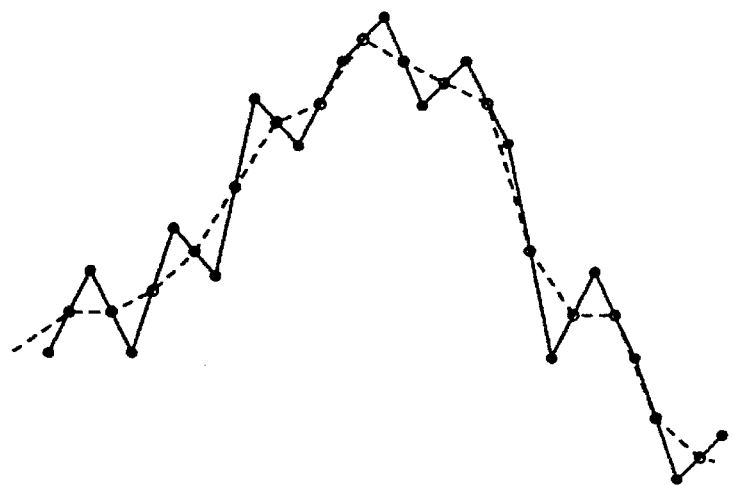
FIG. 6 is a diagram explaining still another embodiment of a pixel data smoothing method.
Figure 7:
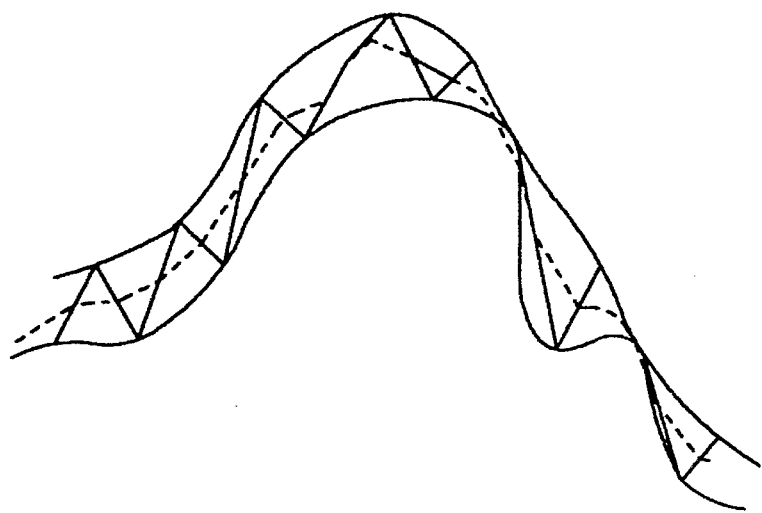
FIG. 7 is a diagram explaining a further embodiment of a pixel data smoothing method.

The smoothing methods include a smoothing method which interconnects the peaks of a signal intensity profile as shown in FIG. 4, a smoothing method which interconnects the bottoms of a signal intensity profile as shown in FIG. 5, a smoothing method which interconnects the middle points between peak and bottom of a signal intensity profile as shown in FIG. 6, a smoothing method which uses a so-called moving average method as shown in FIG. 7, and other methods. Any one of these methods may be used.

Figure 8A:
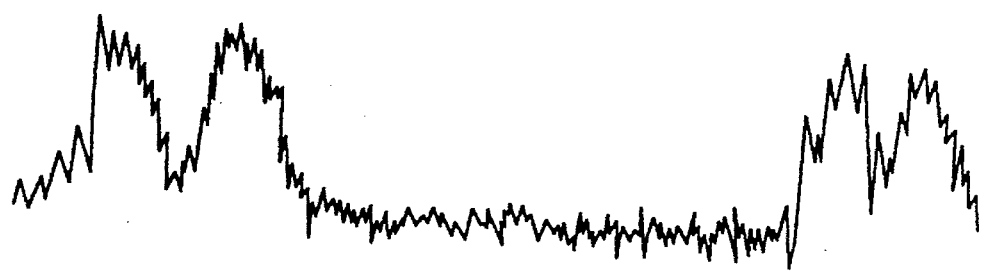
FIG. 8A shows a signal intensity profile before smoothing.
Figure 8B:
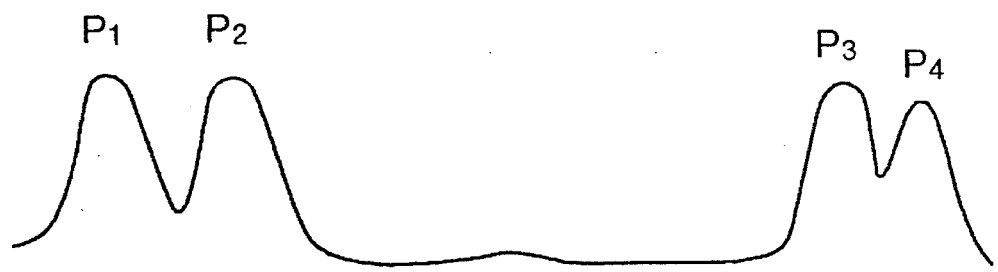
FIG. 8B shows a signal intensity profile after smoothing.

The signal intensity profile is smoothed by the smoothing circuit 12 as shown in FIG. 8B, and has a very gentle curve as compared to the profile before smoothing as shown in FIG. 8A.

The smoothed signal intensity profiles are inputted to a shift register 13.

This shift register 13 is a one-dimensional storage which stores sequentially the inputted signal intensity profile of, for example, five addresses.

For example, the brightness values (peak values) of five pixels of the smoothed signal intensity data (1) to (5) shown in FIG. 4 are sequentially stored from the left to the right as viewed in the figure. These brightness values are inputted at the same time to a brightness slope calculation circuit 14.

The brightness slope calculation circuit 14 detects a change in the inputted five brightness values to obtain a maximum value of the signal intensity profile, i.e., a value at a transition point from a monotonous increase to a monotonous decrease. At the next clock, the signal intensity data (2) to (6) is checked by the circuit 16 and the data (4) is confirmed to be at the transition point.

In the case of the waveform shown in FIG. 8B, the maximum values $P_1$, $P_2$, $P_3$, and $P_4$ are detected. The addresses of the frame memory 10 corresponding to these maximum values are detected and supplied to the graphics/control/calculation circuit 7.

The graphics/control/calculation circuit 7 selects the maximum values $P_2$ and $P_3$ from the four maximum values $P_1$, $P_2$, $P_3$, and $P_4$, because in this embodiment the inner wall of a ventricle of the heart is detected to calculate the ventricle volume. If the volume of the heart including the outer wall, the maximum values $P_1$ and $P_4$ are selected. Whether the volume is selected or the volume is selected can be designated, for example, by the input unit 6.

In accordance with the selected maximum values $P_2$ and $P_3$, the graphics/control/calculation circuit 7 calculates the line segment lengths in the ventricle of the line segments 30A to 30E shown in FIG. 2.

The graphics/control/calculation circuit 7 calculates the volume of the heart by the following equation by using the areas $A_1$, $A_2$, $A_3$, and $A_4$ calculated by the line segment lengths and a length h between the intersections between the line segment 30E and the line segments 30A and 30D.

$$V = (A_1 + A_2 + A_3)h - A_4 h/2 + \pi h^3 \quad (1)$$

This equation means a volume calculating method called a Simpson method. With this method, an approximate volume of the heart can be calculated.

Figure 9:
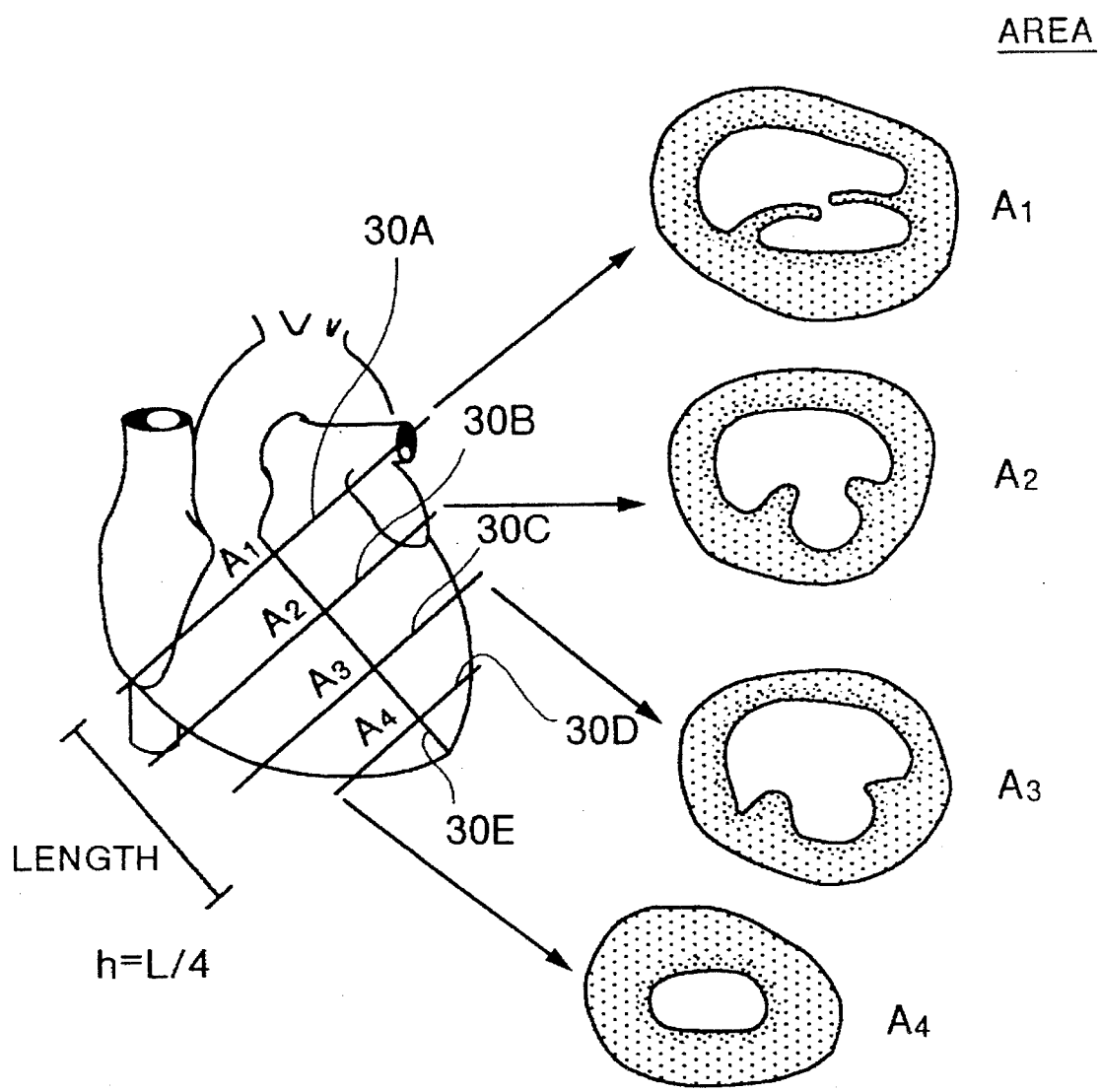
FIG. 9 is a diagram explaining a Simpson method.

FIG. 9 helps understand the volume calculating method. The details of this method is to be referred to Wyatt, HL, et al., Circulation 60:1104, pp. 310–317, (1979). This document is incorporated herein by reference.

The graphics display unit 9 selects numeric characters corresponding to the calculated volume values, and the numeric data is supplied via the synthesizer 4 to the display device 5 to display it in an area 5B shown in FIG. 2. If the sectional area of the heart having the two-dimensional echogram of FIG. 2 is calculated instead of calculating the volume, the area value is displayed in the area 5B.

In the ultrasonic diagnostic apparatus of this embodiment, the signal intensity profile of image data along a designated line segment is smoothed, and thereafter the change degree of the profile along the line segment is detected to judge a boarder of an organ in accordance with the maximum values of the profile, i.e., in accordance with transition points from a monotonous increase to a monotonous decrease.

Accordingly, a fault judgement to be caused by noises can be eliminated. This judgement is not affected by different signal intensities of patients so that a correct judgement is ensured for all patients.

The change degree of the profile can be detected even if an organ changes its size. Therefore, a correct judgement is ensured even for a moving organ.

In this embodiment, the coordinates of the points $P_2$ and $P_3$ (refer to FIG. 8B) obtained by the brightness slope calculating circuit 14 and graphics/control/calculation circuit 7 are displayed as block signs superposed upon the two-dimensional echogram as shown in FIGS. 2 and 3. An operator can therefore check whether the volume value displayed in the area 5B has been calculated in accordance with the correct lengths of the line segments 30A to 30E.

Figure 12:
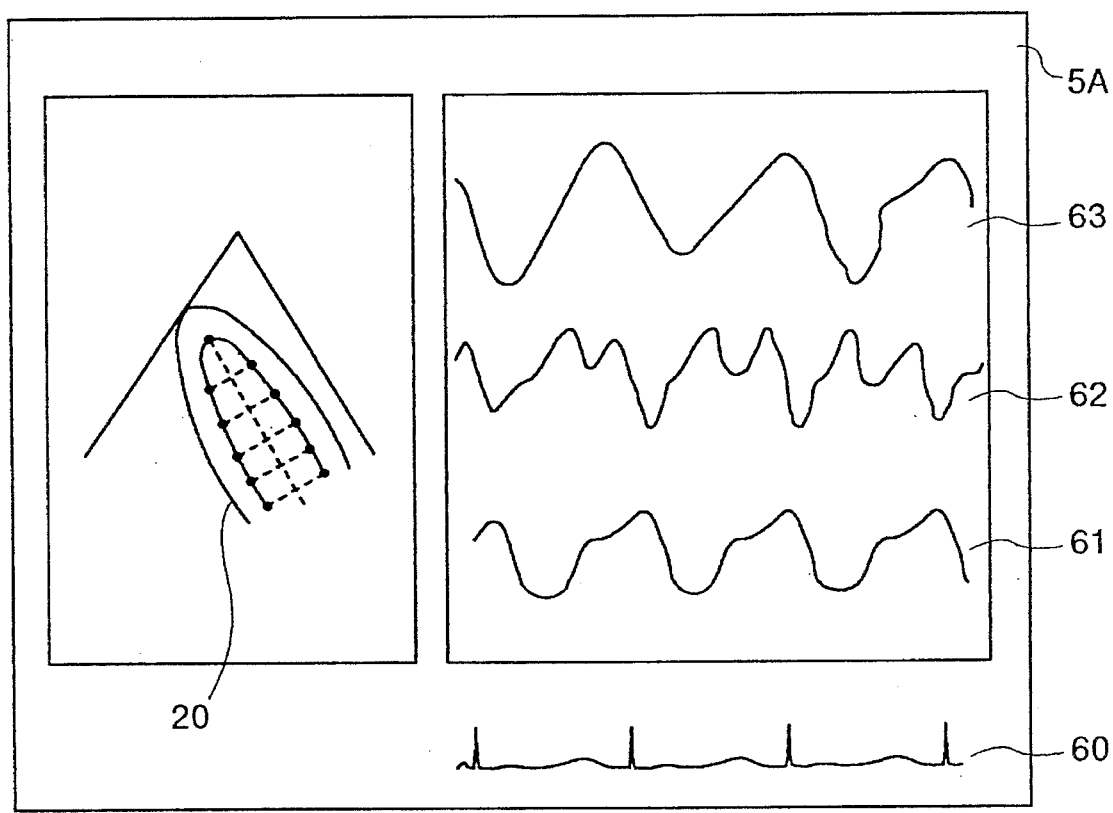
FIG. 12 is a diagram showing an example of a display on the display device of the ultrasonic diagnostic apparatus shown in FIG. 11.
Figure 13:
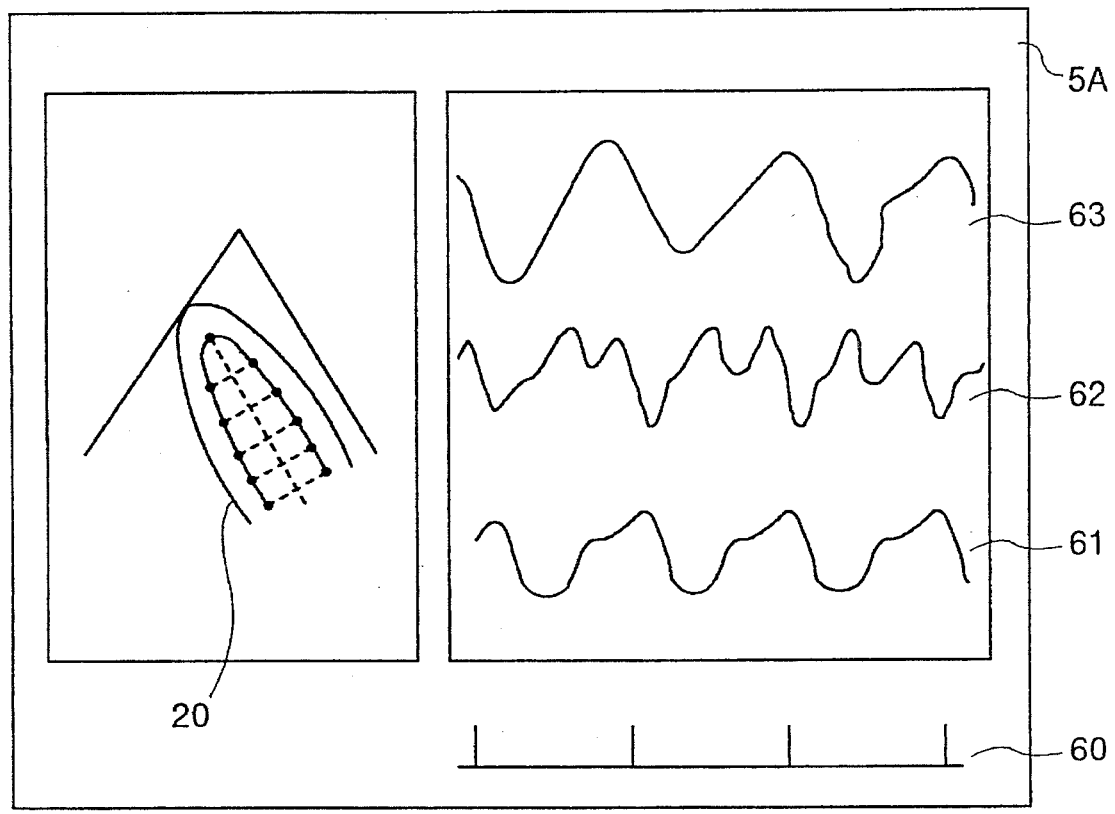
FIG. 13 is a diagram showing another example of a display on the display device of the ultrasonic diagnostic apparatus shown in FIG. 11.
Figure 14:
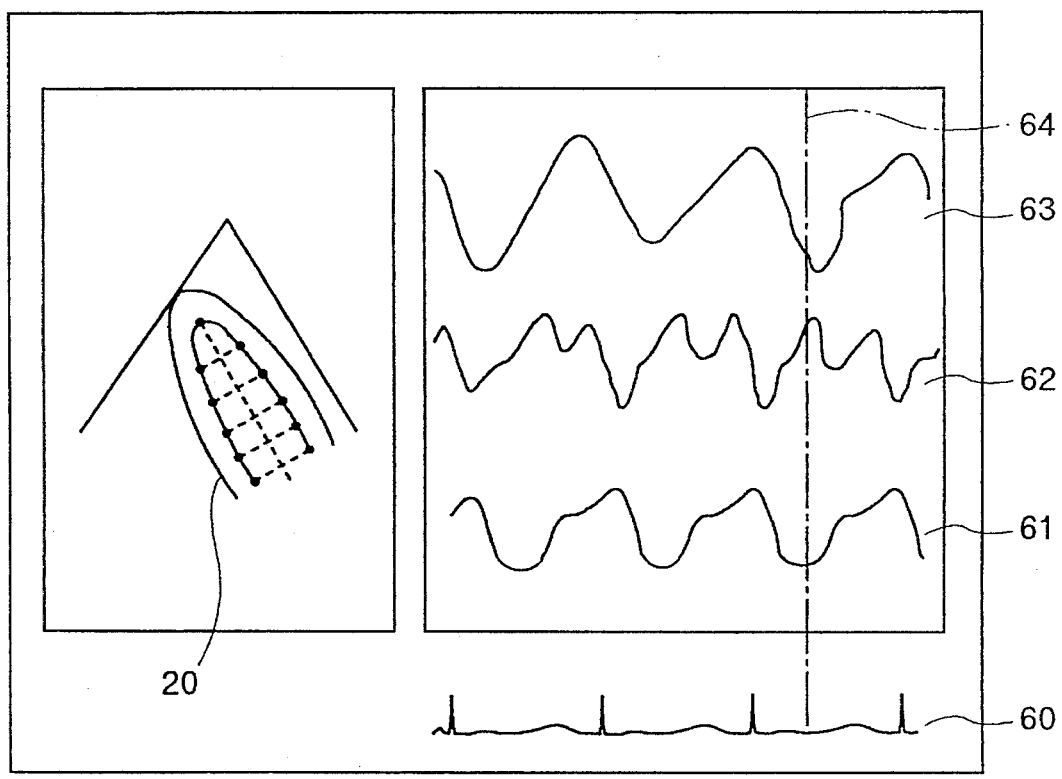
FIG. 14 is a diagram showing still another example of a display on the display device of the ultrasonic diagnostic apparatus shown in FIG. 11.

Instead of displaying the points $P_2$ and $P_3$ by block signs, the brightness or color of these points may be changed from the other area to allow an operator to visually check them. Alternatively, these points may be displayed by circles as shown in FIGS. 12 to 14.

The points $P_2$ and $P_3$ of the line segments 30A to 30E are generally on an elliptical line. Therefore, a function representing the ellipse is predetermined, and if there is any point $P_2$ or $P_3$ greatly shifted from the function, i.e., if there is any point which shifts from the function in excess of a preset threshold value, such a point is linearly interpolated by adjacent points. The interpolated point is displayed on the two-dimensional echogram so as to be easily discriminated from the other points. In this case, the volume value is calculated by using the interpolated point.

Figure 10:
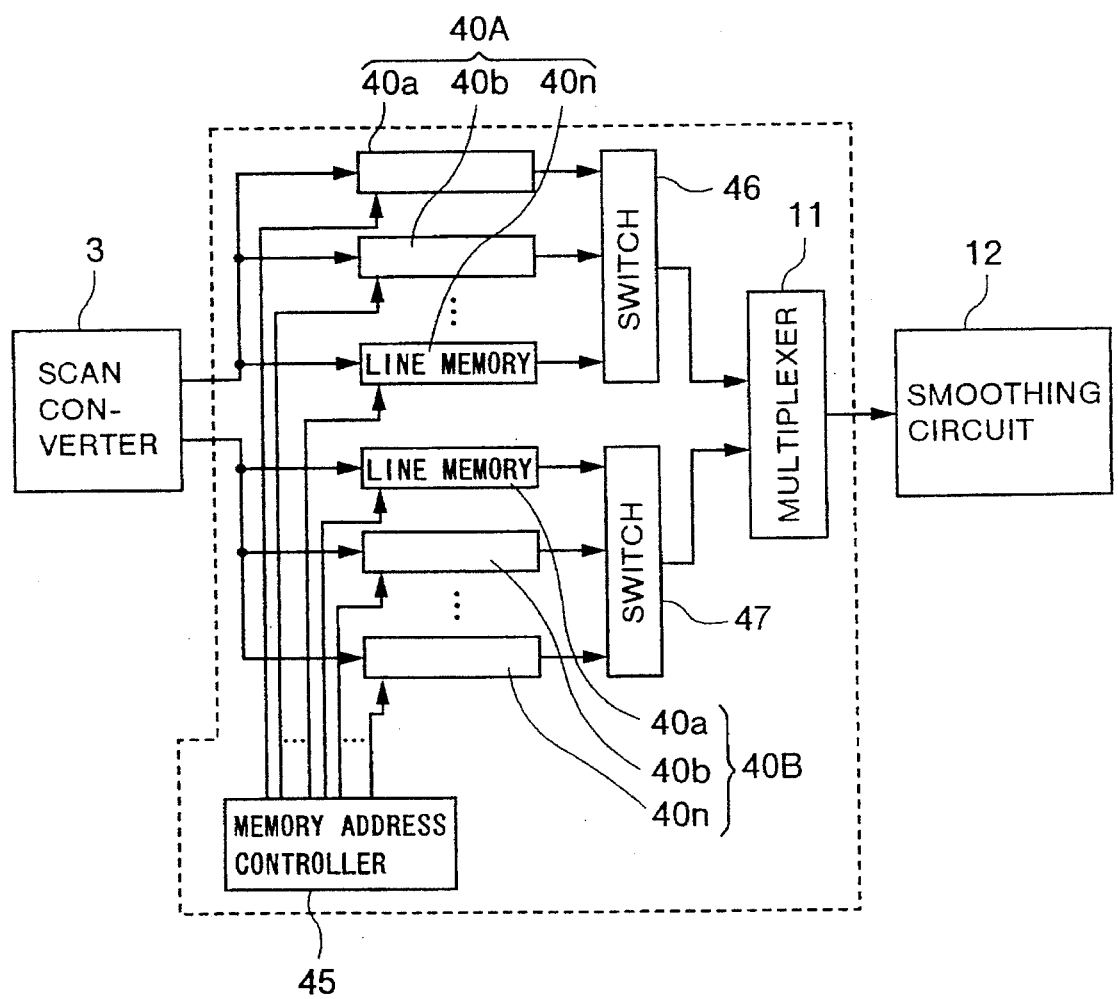
FIG. 10 is a block diagram showing the structure of an ultrasonic diagnostic apparatus according to another embodiment of the invention.

FIG. 10 is a block diagram showing another embodiment of the circuit portion surrounded by a broken line in FIG. 1, and identical reference numerals to those shown in FIG. 1 represent the elements having similar functions.

Pixel image data along designated line segments 30A to 30D supplied from the digital scan converter 3 is inputted to a line memory 40 under the control of a line memory address controller 45.

The line memory 40 is constituted by two line memory groups 40A and 40B each corresponding to one frame.

For example, the signal intensity profile of the image data indicated at (a) of FIG. 3 is inputted to a line memory 40a of the line memory group 40A, and the signal intensity profile of the image data indicated at (b) of FIG. 3 is inputted to a line memory 40b.

The signal intensity profiles from the line memory groups are sequentially inputted via switches 46 and 47 and a multiplexer 11 to the smoothing circuit 12.

In the above-described embodiments, the boarder of an organ is judged to correspond to an extreme value of image data. Obviously, the boarder may be judged to correspond to a point near the extreme value. In other words, the boarder may be judged by using the extreme value as a judgement reference. Similarly, this judgement may also be performed in accordance with the change degree of a signal intensity profile.

In the above embodiments, the directions of the designated line segments are not the same as those of ultrasonic beams and have an angle tilted from the beam angles. The directions of the designated line segments are not limited to this, but obviously they may be coincident with the beam angles.

In the above embodiments, the subject to be diagnosed is a heart which continuously changes its size. The subject is not limited to this, but obviously an organ which does not change its size may also be used as the subject.

In the above embodiments, a sector scan probe is used as the ultrasonic probe. The probe is not limited to the sector scan probe, but obviously it may be a linear scan probe.

2nd Embodiment

Figure 11:
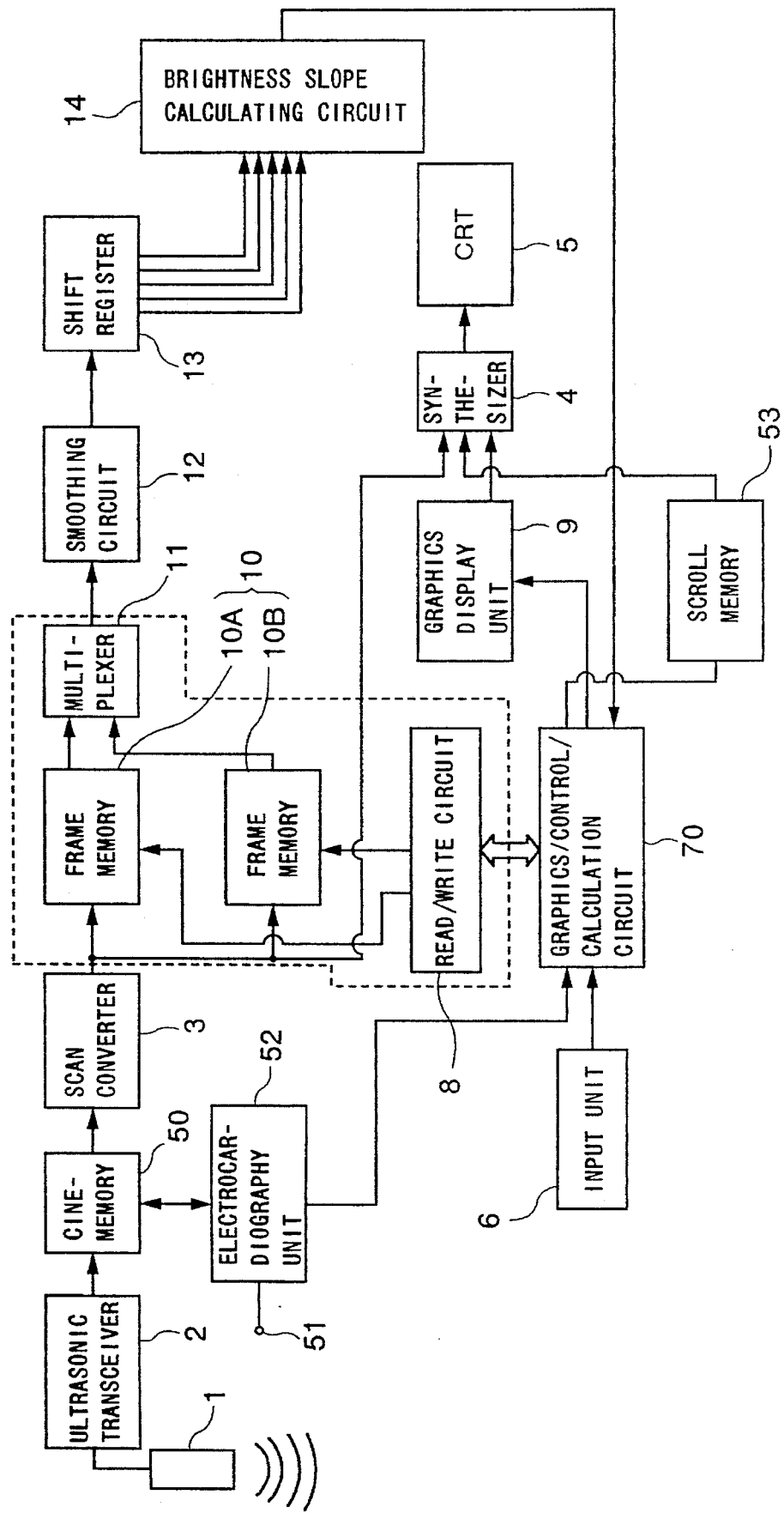
FIG. 11 is a block diagram showing the structure of an ultrasonic diagnostic apparatus according to still another embodiment of the invention.

FIG. 11 is a block diagram showing an ultrasonic diagnostic apparatus according to the second embodiment of the invention. Identical reference numerals to those shown in FIG. 1 represent the elements having similar functions.

The structure different from FIG. 1 is a cine-memory 50 interposed between the ultrasonic transceiver 2 and the digital scan converter 3.

The cine-memory 50 sequentially stores one frame after another of reflected ultrasonic beams or echoes (US line data) received at the ultrasonic probe 1. Therefore, when an electrocardiogram is displayed in accordance with signals from ECG electrodes 1, the echo data can be synchronized with the electrocardiogram as will be described later. Instead of the electrocardiogram, an electrocardiopressuregram or an electrocardiophonogram may be used by a known method. Each waveform image can be displayed synchronously with the echo data.

The cine-memory 50 has also a function of a buffer to the next stage digital scan converter 3.

A graphics/control/calculation circuit 70 has the following functions other than those of the graphics/control/calculation circuit 7 shown in FIG. 1.

The graphics/control/calculation circuit 70 generates an electrocardiogram in accordance with an output from an electrocardiography unit 52. The electrocardiogram data is supplied via a scroll memory 53 and synthesizer 4 to the display unit 5. The electrocardiogram and a two-dimensional echogram are displayed on the same screen, with the electrocardiogram being scrolled synchronously with the motion of the heart image 20 of two-dimensional echogram.

The graphics/control/calculation circuit 70 calculates the volume of the heart 20 in accordance with the outputs from the brightness slope calculating circuit 14, and generates a graph showing a time sequential change in the volume. This graph data is supplied via the scroll memory 53 and synthesizer 4 to the display unit 5. The graph and the two-dimensional echogram are displayed on the same screen, with the graph being scrolled synchronously with the motion of the heart image 20 of two-dimensional echogram.

In this manner, the change in the volume of an organ can be displayed as an image of waveform which changes with time. Accordingly, a reliable and correct changing waveform can be displayed so that the change in the motion of an organ can be more clearly observed.

The graphics/control/calculation circuit 7 generates a graph showing a time sequential change in a volume change factor Vd/dt which is obtained by differentiating the volume of the heart 20 relative to time t. This graph data is supplied via the scroll memory 53 and synthesizer 4 to the display unit 5. The graph and the two-dimensional echogram are displayed on the same screen, with the graph being scrolled synchronously with the motion of the heart image 20 of two-dimensional echogram.

In this manner, the time sequential change in the volume change factor can be observed clearly at once. Therefore, a fine motion of an organ can be observed contributing to diagnosing the organ.

The graphics/control/calculation circuit 70 calculates the velocities of the heart 20 during the systole and diastole periods in accordance with the time sequential change in the lengths of the line segments, both ends thereof being terminated at the boarder of the heart 20, in the manner similar to the first embodiment. The circuit 70 also calculates the acceleration velocities in accordance with a change in the velocities. The circuit 70 also calculates a pressure at each line segment by multiplying the acceleration velocity by a proper weight.

The graphics/control/calculation circuit 70 generates a graph showing a time sequential change in the pressure. This graph data is supplied via the scroll memory 53 and synthesizer 4 to the display unit 5. The graph and the two-dimensional echogram are displayed on the same screen, with the graph being scrolled synchronously with the motion of the heart image 20 of two-dimensional echogram.

The graphic/control/calculation circuit 70 operates to display the electrocardiogram and these graphs at the same time on the same screen synchronously with each other. FIG. 12 shows an example of such a display on the display device 5.

In FIG. 12, on the right side area of the display screen 5A, an electrocardiogram 60 and other graphs 61 to 63 are displayed from the upper area to the lower area of the screen in this order synchronously with each other. The graph 61 indicates the volume of the heart 20, the graph 62 indicates the change factor of the volume, and the graph 63 indicates the pressure.

FIG. 13 shows another example of a display on the display device 5 in which an electrocardiogram 60 shows its R-waves in particular.

FIG. 14 shows another example of a display in which a line 64 showing the same time at each graph is displayed for facilitating the time sequential correspondence between an electrocardiogram 60 and other graphs 61 to 63.

The line 64 can be set to an arbitrary timing by operating the input unit 6.

3rd Embodiment

Next, the third embodiment will be described with reference to FIGS. 15 to 20.

Figure 15:
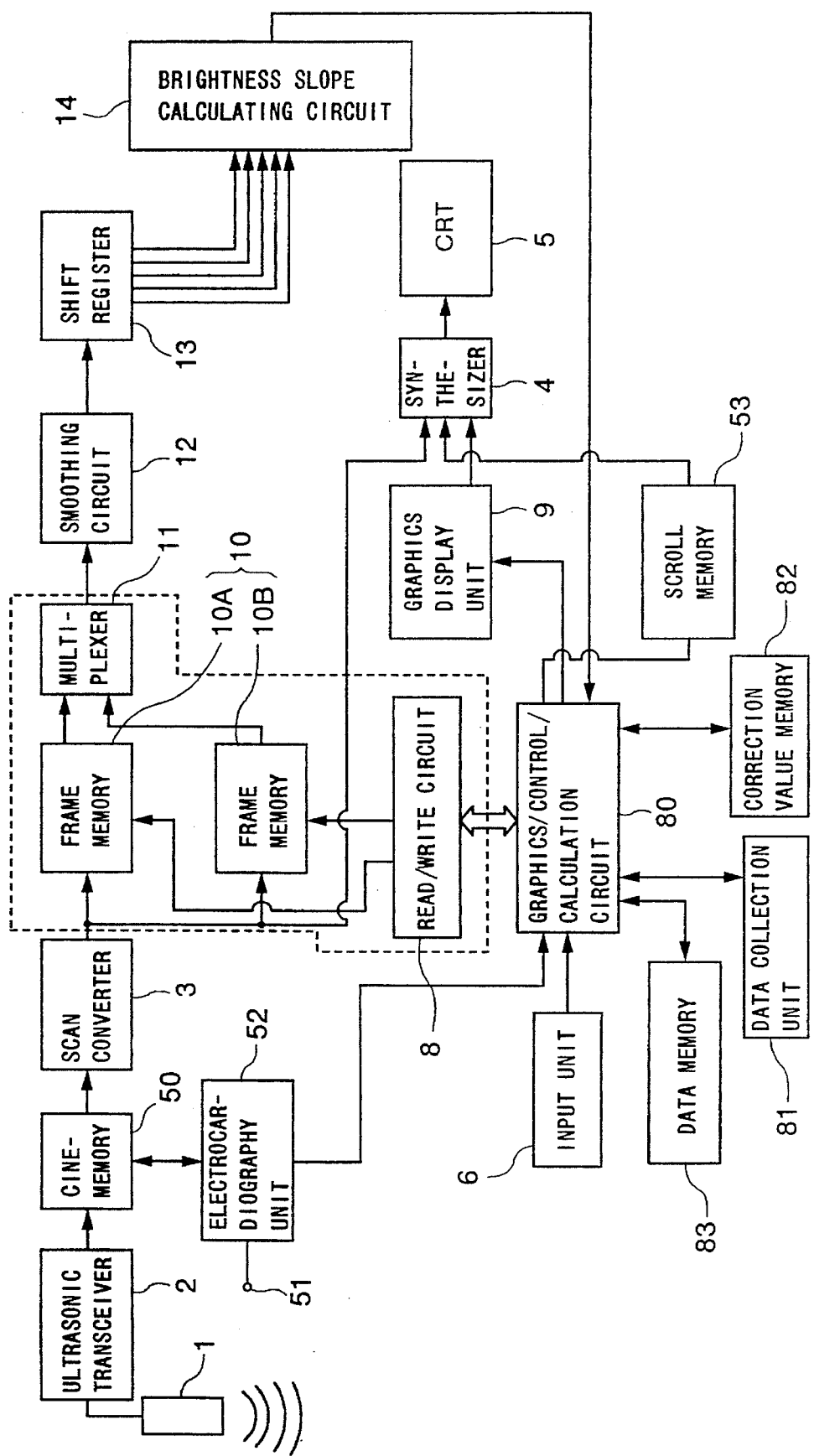
FIG. 15 is a block diagram showing the structure of an ultrasonic diagnostic apparatus according to another embodiment of the invention.

FIG. 15 shows the structure of an ultrasonic diagnostic apparatus according to the third embodiment. Like elements to those shown in FIG. 11 are represented by using identical reference numerals, and the description thereof is omitted. The apparatus of this embodiment is provided with a data correction unit 81, a correction value memory 82, and a data memory 83. The apparatus is adapted to normalize data of the A-mode. The graphics/control/calculation circuit 80 has both a function of calculating correction values to be stored in the adjusted value memory 82 and a function of correcting a set of data 84 by using a corresponding correction value.

Figure 16:
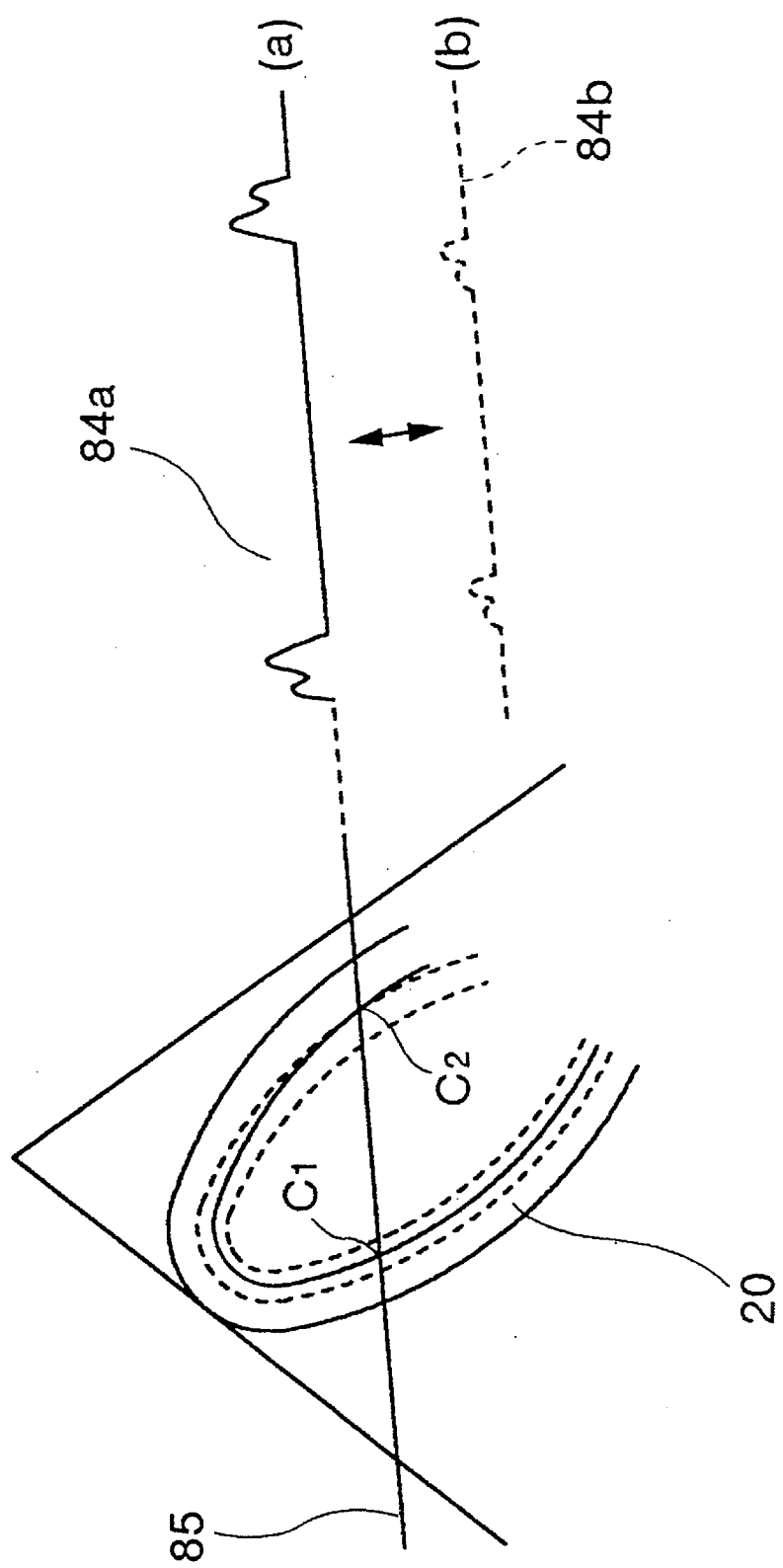
FIG. 16 shows an example of a display on the display device.

The intensity of data of the A-mode generally changes with the motion of a heart. For example, as shown in FIG. 16, as a heart image 20 changes from diastole (solid line) to systole (broken line), data of the A-mode changes from that indicated at (a) to that indicated at (b). The width of echo data at a high brightness corresponding to the myocardium changes as the heart moves, and the brightness becomes high during the diastole period and low during the systole period.

Figure 17:
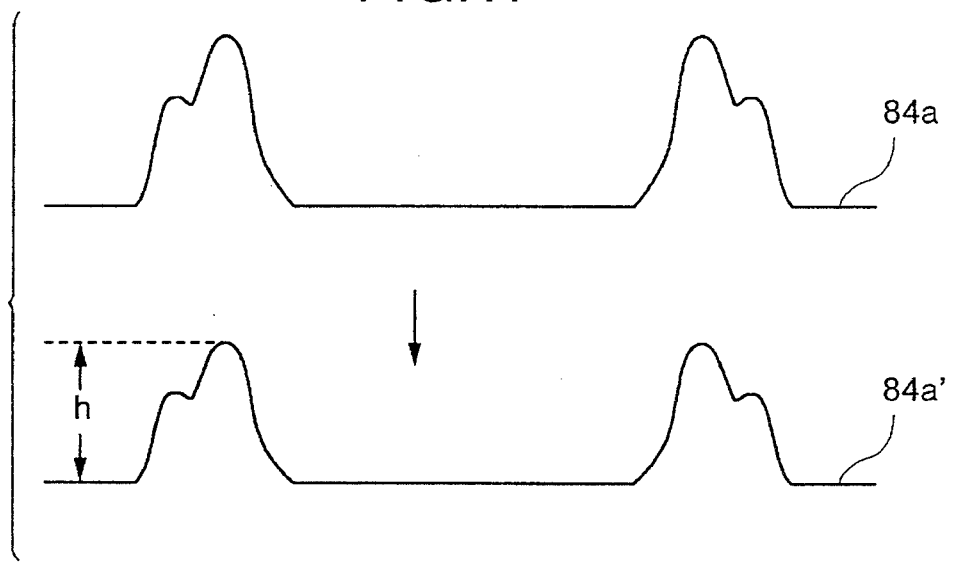
FIGS. 17 and 18 illustrate normalization of signal intensity profiles of image data.
Figure 18:
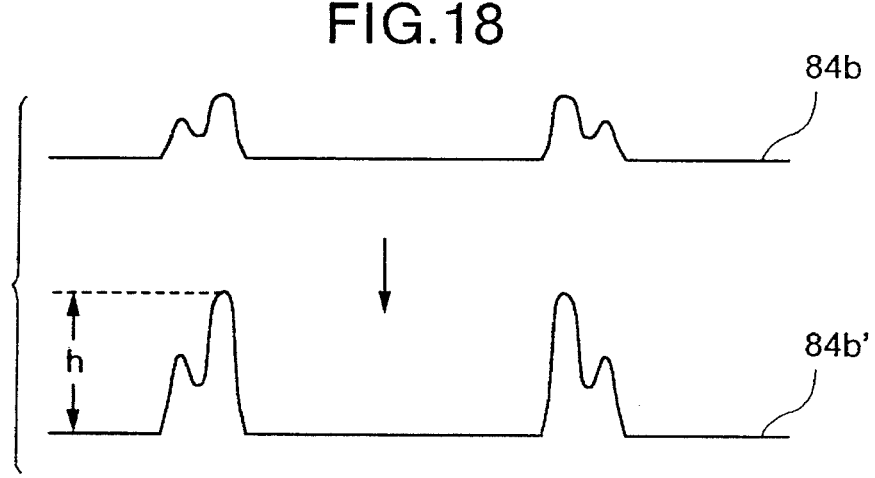

The graphics/control/calculation circuit 80 stores the data 84 in the data memory 83, and calculates a ratio of the maximum brightness in the profile to a preset reference brightness (as indicated at (h) in FIGS. 17 and 18) to store the ratio in the correction memory 82 as a correction value. The data 84 in the memory 83 is read and multiplied by the corresponding correction value. In this manner, the peak values of data 84*a* and 84*b* of two profiles become coincident. In other words, the profiles of the data 84*a* and 84*b* are normalized. The data correction method is not limited to such normalization. For example, only when the peak brightness is lower than the reference brightness, the data 84 may be corrected so as to make the peak brightness have the reference brightness or have the reference brightness multiplied by a predetermined factor. In this case, the data having a peak brightness higher than the reference brightness is not corrected.

By normalizing data of the A-mode, the volume of a heart can be calculated more precisely.

The normalizing process is performed for data of the A-mode after the data is smoothed in the circuit structure shown in FIG. 15. Obviously, the normalizing process may be performed for the data before smoothing. If the motion of the heart is being monitored by the electrocardiography unit 52, the image data may be normalized synchronously with the motion of the monitored heart. For example, only when the heart is in a systole state, the image data is amplified by a predetermined amplification factor.

Figure 19:
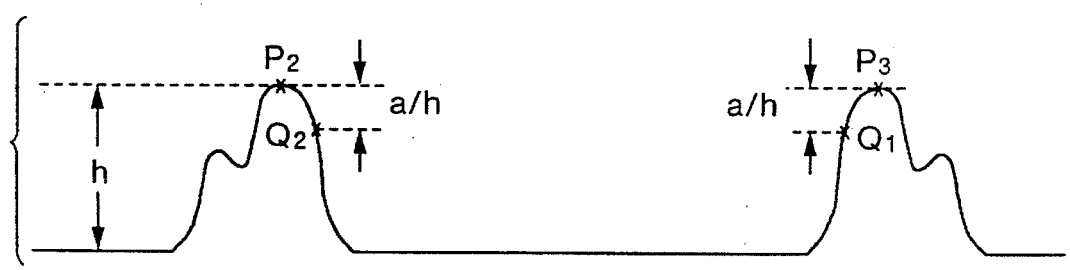
FIG. 19 illustrates an embodiment of a method of identifying a pair of intersections.

In this embodiment, of maximum values obtained by the brightness slope calculation circuit 14, the maximum values $P_2$ and $P_3$ shown in FIG. 19 are selected by a graphics/control/calculation circuit 80. The circuit 80 also obtains the addresses of brightness values $Q_1$ and $Q_2$ obtained by subtracting a predetermined fraction a/h (a fraction determined from the rule of thumb, for example, at 95%) from the brightness values of the maximum values $P_2$ and $P_3$.

The addresses of the brightness values $Q_1$ and $Q_2$ corresponding to contour points $C_1$ and $C_2$ of the myocardium on the ventricle/atrium side along the A-mode data deriving line 85 of the heart image 20 shown in FIG. 16.

In this manner, the contour points of the myocardium on the ventricle/atrium side are judged from the corrected brightness values, for example, to be the points shifted from the maximum brightness toward the ventricle/atrium side by a predetermined fraction.

Figure 20:
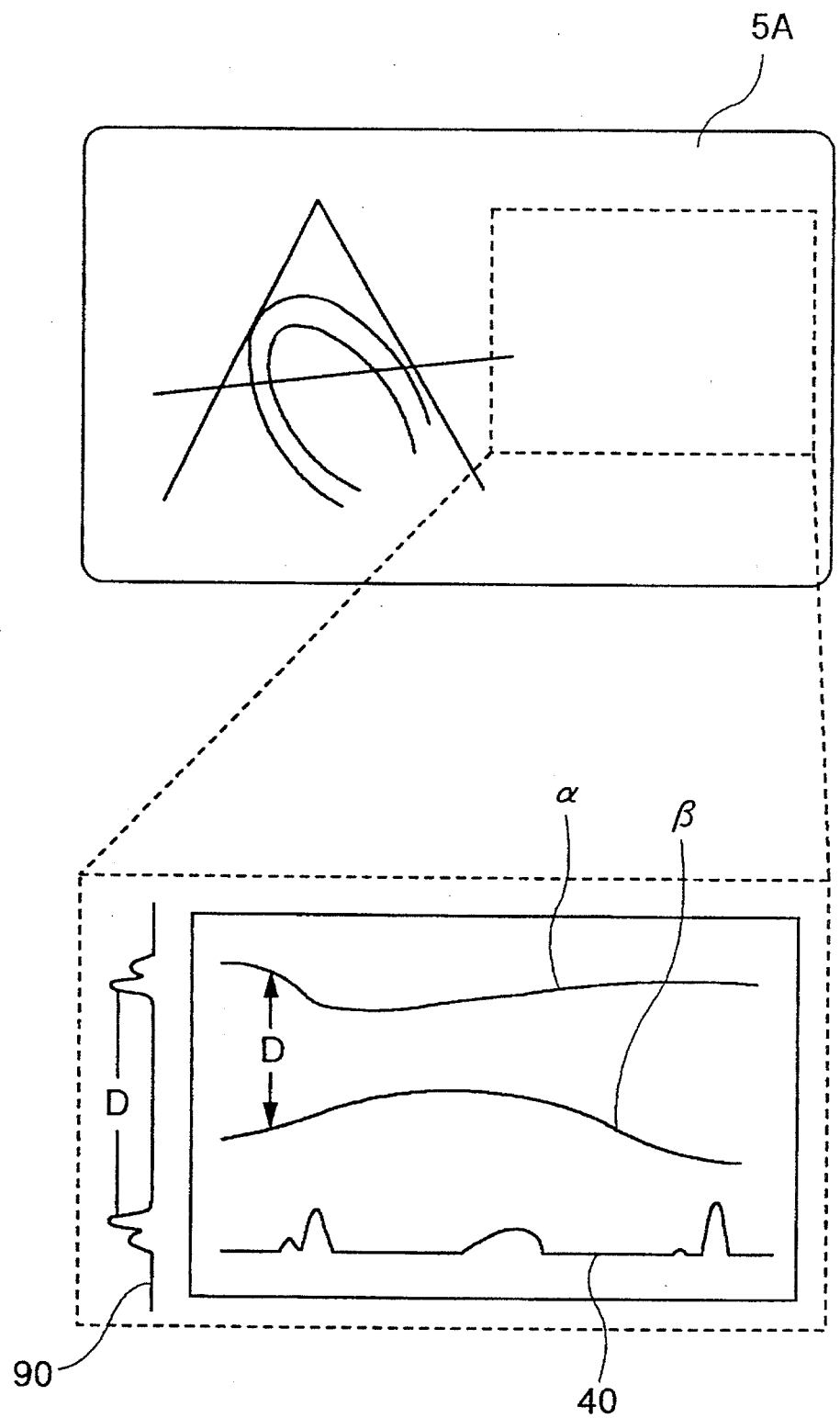
FIG. 20 is a diagram showing an example of a display on the display device.

As shown in FIG. 20, the graphics/control/calculation circuit 80 operates to display graphs α and β on the display screen 5A of the display device 5 at the right side of the two-dimensional echogram. The graph α shows a time sequential change of the point $Q_1$ with the motion of the heart image 20, and the graph β shows a time sequential change of the point $Q_2$ with the motion of the heart image 20. By observing the graphs α and β, it becomes possible to readily check the state of the time sequential motion of the points $Q_1$ and $Q_2$ which are moving toward each other or apart from each other.

An electrocardiogram 40 is also displayed on the display screen 5A in correspondence with the time axes of the graphs α and β. The electrocardiogram 40 is generated in the following manner.

Signals from the ECG electrodes 51 in contact with the subject body are supplied via the electrocardiography unit 52 to the graphics/control/calculation circuit 80. This circuit 80 fetches data such as beam scan time data (related to a motion of a heart) readable from the cine-memory 50, and displays the electrocardiogram 40 synchronously with the time data.

By displaying the graphs α and β synchronously with the electrocardiogram 40 in the above manner, the graphs α and β can be checked precisely.

In FIG. 20, a waveform 90 indicates the brightness on the A-mode data deriving line 85 displayed in the manner same as conventional, the brightness being displayed after being normalized in accordance with the motion of the heart.

In the ultrasonic diagnostic apparatus of the embodiment, the brightness data along the A-mode data deriving line designated traversing a heart is obtained and normalized both during the diastole and systole periods of the heart.

In this manner, the contour points of the myocardium on the ventricle/atrium side are judged from the normalized brightness values, for example, to be the points shifted from the maximum brightness toward the ventricle/atrium side by a predetermined fraction.

Such judgement can therefore be performed uniformly and with ease both during the diastole and systole periods of the heart, providing a precise calculation of contour points.

4th Embodiment

The fourth embodiment uses the same circuit structure shown in FIG. 15. Data stored in the cine-memory 50 is read in a slow mode by the graphics/control/calculation circuit 80 to display it on the display device 5 in slow motion. That is to say, the B-mode display is performed in slow motion. In this case, the brightness of the B-mode data is also normalized similar to the normalization of the brightness of the A-mode data of the third embodiment. Accordingly, generally speaking, a two-dimensional echogram of a heart can be brightly and clearly displayed, which otherwise is likely to be displayed dark during the systole period.

If data from the electrocardiography unit 52 and cine-memory 50 is synchronized, the systole state of a heart may be judged from the electrocardiogram, and the brightness during the systole period may be amplified by a predetermined amplification factor.

What is claimed is:

1. An ultrasonic diagnostic apparatus comprising:

means for radiating an ultrasonic wave to a patient and receiving a reflected ultrasonic wave;

means for generating a real time two-dimensional echogram of an organ from said reflected, received ultrasonic wave and displaying said real time two-dimensional echogram on a display device;

means for designating a line segment on said display device;

means for obtaining a pair of intersections between the wall of said two-dimensional echogram and said line segment;

means for measuring the length between said pair of intersections;

means for calculating the area of a cross section of said organ and/or said volume of said organ, by using said measured length; and means for displaying said calculated area and/or volume on said display device, wherein said area and/or said volume is calculated and displayed substantially in real time.

2. An ultrasonic diagnostic apparatus according to claim 1 further comprising:

a first memory for storing first pixel data of at least a portion, superposed upon said line segment, of a first two-dimensional echogram; and a second memory for storing second pixel data of at least a portion, superposed upon said line segment, of a second two-dimensional echogram generated following said first two-dimensional echogram, wherein while said second pixel data is written in said second memory, said area and/or said volume is calculated and displayed in accordance with said first pixel data stored in said first memory.

3. An ultrasonic diagnostic apparatus according to claim 1 further comprising means for display the positions of said obtained intersections on said two-dimensional echogram substantially in real time.

4. An ultrasonic diagnostic apparatus according to claim 1, wherein said means for obtaining said intersections comprises:

means for reading a signal intensity of said two-dimensional echogram at the portion superposing said line segment and forming a first signal intensity profile;

means for smoothing said first signal intensity profile to form a second signal intensity profile;

means for obtaining inflection points of said second signal intensity profile; and means for determining said pair of intersections corresponding to the wall of said organ, from said obtained maximum value.

5. An ultrasonic diagnostic apparatus according to claim 4, wherein said means for forming said second signal intensity profile forms said second signal intensity profile by using the envelope of said first signal intensity profile.

6. An ultrasonic diagnostic apparatus according to claim 4, wherein said means for forming said second signal intensity profile forms said second signal intensity profile by subjecting said first signal intensity profile to a moving average process.

7. An ultrasonic diagnostic apparatus according to claim 4 further comprising means for normalizing said first or second signal intensity profile.

8. An ultrasonic diagnostic apparatus according to claim 4 further comprising:

means for normalizing said second signal intensity profile to form a third signal intensity profile; and means for identifying as said intersections a pair of points having a signal intensity smaller by a predetermined fraction than a pair of inflection points of said third signal intensity profile, said pair of points being positioned toward the inside of the positions corresponding to said pair of inflection points.

9. An ultrasonic diagnostic apparatus according to claim 1 further comprising:

means for subjecting each said intersection to a predetermined function representing the shape of the wall of said organ, and correcting the coordinates of each said intersection not matching said function in accordance with other intersections matching said function; and means for displaying said intersection with corrected coordinates on said display device.

10. An ultrasonic diagnostic apparatus according to claim 1, wherein said display means displays a change in the volume of said organ in the form of waveform.

11. An ultrasonic diagnostic apparatus according to claim 10 further comprising:

means for obtaining a change rate of said volume; and means for displaying said change rate in the form of waveform.

12. An ultrasonic diagnostic apparatus according to claim 10 further comprising:

means for monitoring the motion of said organ and forming a motion waveform; and means for synchronously displaying the motion waveform of said organ and the change rate waveform of said volume of said organ.

13. An ultrasonic diagnostic apparatus according to claim 12, wherein said means for forming said motion waveform forms an electrocardiogram of a heart.

14. An ultrasonic diagnostic apparatus comprising:

means for radiating an ultrasonic wave to a patient and receiving a reflected ultrasonic wave;

means for generating image data necessary for obtaining a moving image of a two-dimensional echogram of the heart from said reflected, received ultrasonic wave;

a cine-memory for storing said image data;

means for monitoring the motion of said heart;

means for generating the moving image of said two-dimensional echogram by processing said image data, said image data being amplified to have a high brightness during a systole period of said heart; and means for displaying the moving image of said two-dimensional echogram in slow motion.

15. An ultrasonic diagnostic apparatus according to claim 14, wherein said monitoring means monitors the motion of said heart in accordance with an electrocardiogram, an electrocardiopressuregram, or an electrocardiophonogram.

16. An ultrasonic diagnostic apparatus according to claim 14, wherein said monitoring means monitors the motion of said heart in accordance with a change in a signal intensity of said image data.

17. An ultrasonic diagnosis method comprising the steps of:

radiating an ultrasonic wave to a patient and receiving a reflected ultrasonic wave;

generating a real time two-dimensional echogram of an organ from said reflected, received ultrasonic wave and displaying said real time two-dimensional echogram on a display device;

designating a line segment on said display device;

obtaining a pair of intersections between the wall of said two-dimensional echogram and said line segment;

measuring the length between said pair of intersections;

calculating the area of a cross section of said organ and/or the volume of said organ, by using said measured length; and displaying said calculated area and/or volume on said display device, wherein said area and/or said volume is calculated and displayed substantially in real time.

* * * * *